United States Patent
Sinharay et al.

(10) Patent No.: US 11,331,047 B2
(45) Date of Patent: May 17, 2022

(54) METHOD AND SYSTEM FOR HEALTH MONITORING USING AMPLITUDE MODULATED CONTINUOUS WAVE MICROWAVE SIGNAL

(71) Applicant: Tata Consultancy Services Limited, Mumbai (IN)

(72) Inventors: Arijit Sinharay, Kolkata (IN); Rajat Kumar Das, Kolkata (IN); Sayan Seth, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 699 days.

(21) Appl. No.: 16/285,133

(22) Filed: Feb. 25, 2019

(65) Prior Publication Data

US 2020/0129129 A1    Apr. 30, 2020

(30) Foreign Application Priority Data

Oct. 25, 2018   (IN) .............................. 201821040318

(51) Int. Cl.

| | |
|---|---|
| *A61B 5/0245* | (2006.01) |
| *A61B 5/00* | (2006.01) |
| *A61B 5/08* | (2006.01) |
| *A61B 5/0507* | (2021.01) |
| *A61B 5/0205* | (2006.01) |
| *G01S 13/88* | (2006.01) |
| *G01S 7/288* | (2006.01) |

(52) U.S. Cl.
CPC .......... *A61B 5/7257* (2013.01); *A61B 5/0205* (2013.01); *A61B 5/0245* (2013.01);
(Continued)

(58) Field of Classification Search
CPC ... A61B 5/7257; A61B 5/0205; A61B 5/0245; A61B 5/0507; A61B 5/0816;
(Continued)

(56) References Cited

U.S. PATENT DOCUMENTS 4,958,638 A * 9/1990 Sharpe ................. A61B 5/0205
                                                  600/407
7,811,234 B2   10/2010 McGrath
(Continued)

OTHER PUBLICATIONS

Ebrahim, M. et al. "A Doppler Radar System for Sensing Physiological Parameters in Walking and Standing Positions," Sensors, 2017, vol. 17(3), 485, pp. 1 to 15. (Year: 2017).*
(Continued)

*Primary Examiner* — Amelie R Davis
*Assistant Examiner* — Neshat Baset
(74) *Attorney, Agent, or Firm* — Finnegan, Henderson, Farabow, Garrett & Dunner LLP

(57) ABSTRACT

Health signal monitoring using continuous wave microwave signals is often affected by phase wrapping and null point detection issues. The disclosure herein generally relates to health monitoring, and, more particularly, to a method and a monitoring system for health monitoring using Amplitude Modulated Continuous Wave (AMCW) microwave signals. In this design of the monitoring system, the AMCW microwave signal comprises of a carrier signal and a modulating signal. The modulating signal is used for measuring heart rate and breathing rate of a subject, while the carrier signal is used to tune antenna size in the monitoring system. As the probing wavelength and the antenna size are independent of each other in this design of the monitoring system, the probing wavelength can be adjusted such that effect of the phase wrapping can be minimized. The system addresses the null point measurement problem by quadrature modulating the modulating signal.

6 Claims, 4 Drawing Sheets

(52) U.S. Cl.
CPC .......... *A61B 5/0507* (2013.01); *A61B 5/0816* (2013.01); *A61B 5/7225* (2013.01); *G01S 7/2883* (2021.05); *G01S 7/2886* (2021.05); *G01S 13/88* (2013.01)

(58) Field of Classification Search
CPC ..... A61B 5/7225; A61B 5/113; G01S 7/2883; G01S 7/2886; G01S 13/88; G01S 7/288; G01S 7/415; G01S 13/32; G01S 13/583
See application file for complete search history.

(56) References Cited

U.S. PATENT DOCUMENTS

| | | |
|---|---|---|
| 9,713,434 B2 | 7/2017 | Barak |
| 2008/0077015 A1* | 3/2008 | Boric-Lubecke .... A61B 5/0507 600/453 |
| 2008/0275337 A1* | 11/2008 | Fossan ................ A61B 5/0507 600/428 |
| 2013/0197377 A1* | 8/2013 | Kishi ................... A61B 5/0507 600/508 |
| 2016/0209260 A1* | 7/2016 | Rice ........................ G01S 7/003 |

OTHER PUBLICATIONS

Park, Byung-Kwon, et al. Quadrature demodulation with DC cancellation for a Doppler radar motion detector. Retrieved from the Internet.<URL: https://citeseerx.ist.psu.edu/viewdoc/download?doi=10.1.1.626.4604&rep=rep1&type=pdf><DOI: 10.1.1.626.4604>(Year: 2007).*

* cited by examiner

METHOD AND SYSTEM FOR HEALTH MONITORING USING AMPLITUDE MODULATED CONTINUOUS WAVE MICROWAVE SIGNAL

PRIORITY CLAIM

This U.S. patent application claims priority under 35 U.S.C. § 119 to: India Application No. 201821040318, filed on Oct. 25, 2018. The entire contents of the aforementioned application are incorporated herein by reference.

TECHNICAL FIELD

This disclosure relates generally to health monitoring, and more particularly to a method and a system for health monitoring using Amplitude Modulated Continuous Wave (AMCW) microwave signals.

BACKGROUND

Use of microwave signals for non-contact measurement of heart rate and breathing rate is one of the popular research areas. In some of the existing systems which use microwave signal for health monitoring, continuous wave radar is used. The microwave signal is transmitted towards a user being monitored, and microwave signal which is reflected from the user is further processed. The reflected signal captures vibrational parameters (i.e. due to vibration of heart walls and that of lungs), wherein the vibrational information lies in phase of the signal and sensitivity varies based on wavelength of the microwave signal being used. However, the single channel systems suffer from two disadvantages namely null-point measurement and phase wrapping.

The inventors here have recognized several technical problems with such conventional systems, as explained below. A dual channel measurement can address issues due to null-point measurement. However phase-wrapping problem may still exist if vibrational amplitude of object being probed (for example, chest wall of the user) exceeds a certain threshold as compared to a probing wavelength. In case both the heart rate as well as the breathing rate are being measured, then corresponding vibration is composed of two oscillations of different frequencies (i.e. of the heart rate measurement and that of the breathing rate measurement). In this scenario, breathing rate amplitude may create harmonics that leak into heart rate region, thus causing phase wrapping.

One way to reduce the phase wrapping problem is by increasing the probing wavelength. However sensitivity reduces as the probing wavelength increases, and as a result tiny heart movements may not be picked up while probing. Reducing the probing wavelength to increase the sensitivity introduces phase wrapping from the breathing rate measurement (due to larger chest wall movements) and produces unwanted frequency components in the heart rate region. This puts a restriction on selection of the probing wavelength, and the restriction on the probing wavelength in turn puts constraint on antenna size.

SUMMARY

Embodiments of the present disclosure present technological improvements as solutions to one or more of the above-mentioned technical problems recognized by the inventors in conventional systems. For example, in one embodiment, a method for health monitoring is provided. In this method, an Amplitude Modulated Continuous Wave (AMCW) microwave signal is transmitted towards a subject being monitored, by a monitoring system, wherein the AMCW signal comprises a Continuous Wave (CW) microwave signal as a carrier signal along with a modulating signal. Further, the AMCW microwave signal is captured when reflected back from the subject, by the monitoring system, wherein the modulating signal of the reflected AMCW microwave signal carries heart rate measurement and breathing rate measurement of the subject. Further, from the captured AMCW microwave signal, the modulating signal is extracted by the monitoring system. Further, a first mixed signal (I) is generated by mixing the extracted modulating signal with a reference modulating signal, by the monitoring system, wherein the reference modulating signal is the modulating signal that is transmitted towards the subject. Further, a second mixed signal (Q) is generated by mixing the extracted modulating signal with the quadrature of the reference modulating signal, by the monitoring system. Further, relative phase shift of the modulating signal in the first mixed signal (I) and in the second mixed signal (Q) is captured to generate a relative phase shift signal, by low pass filtering the I and the Q and by taking Arctan on ratio of output of the low pass filtering of the I and the Q, by the monitoring system. Further from the generated relative phase shift signal, a first component and a second component are extracted by the monitoring system, wherein the first component represents the measured heart rate and the second component represents the measured breathing rate of the subject.

In another embodiment, a monitoring system is provided. The monitoring system includes a modulator, an envelope detector, a transmitter antenna, a receiver antenna, a first mixer, a second mixer, a low pass filter, and an extraction module. The monitoring system performs health monitoring of a subject, by executing the following method. Initially, an Amplitude Modulated Continuous Wave (AMCW) microwave signal is transmitted towards a subject being monitored, using a transmitter antenna of a monitoring system, wherein the AMCW signal comprises a Continuous Wave (CW) microwave signal as a carrier signal along with a modulating signal. Further, the AMCW microwave signal is captured when the AMCW microwave signal is reflected from the subject, using a receiver antenna of the monitoring system, wherein the modulating signal of the reflected AMCW microwave signal carries heart rate measurement and breathing rate measurement of the subject. Further, from the captured AMCW microwave signal, the modulating signal is extracted using an envelope detector of the monitoring system. Further, a first mixed signal (I) is generated by mixing the extracted modulating signal with a reference modulating signal, using a first mixer of the monitoring system, wherein the reference modulating signal is the modulating signal that is transmitted towards the subject. Further, a second mixed signal (Q) is generated by mixing the extracted modulating signal with the quadrature of the reference modulating signal, using a second mixer of the monitoring system. Further, relative phase shift of the modulating signal in the first mixed signal (I) and in the second mixed signal (Q) is captured to generate a relative phase shift signal, by low pass filtering the I and the Q and by taking Arctan on ratio of output of the low pass filtering of the I and the Q using a low-pass filter. Further from the generated relative phase shift signal, a first component and a second component are extracted using an extraction module, wherein the first component represents the measured heart rate and the second component represents the measured breathing rate of the subject.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Figure 1:
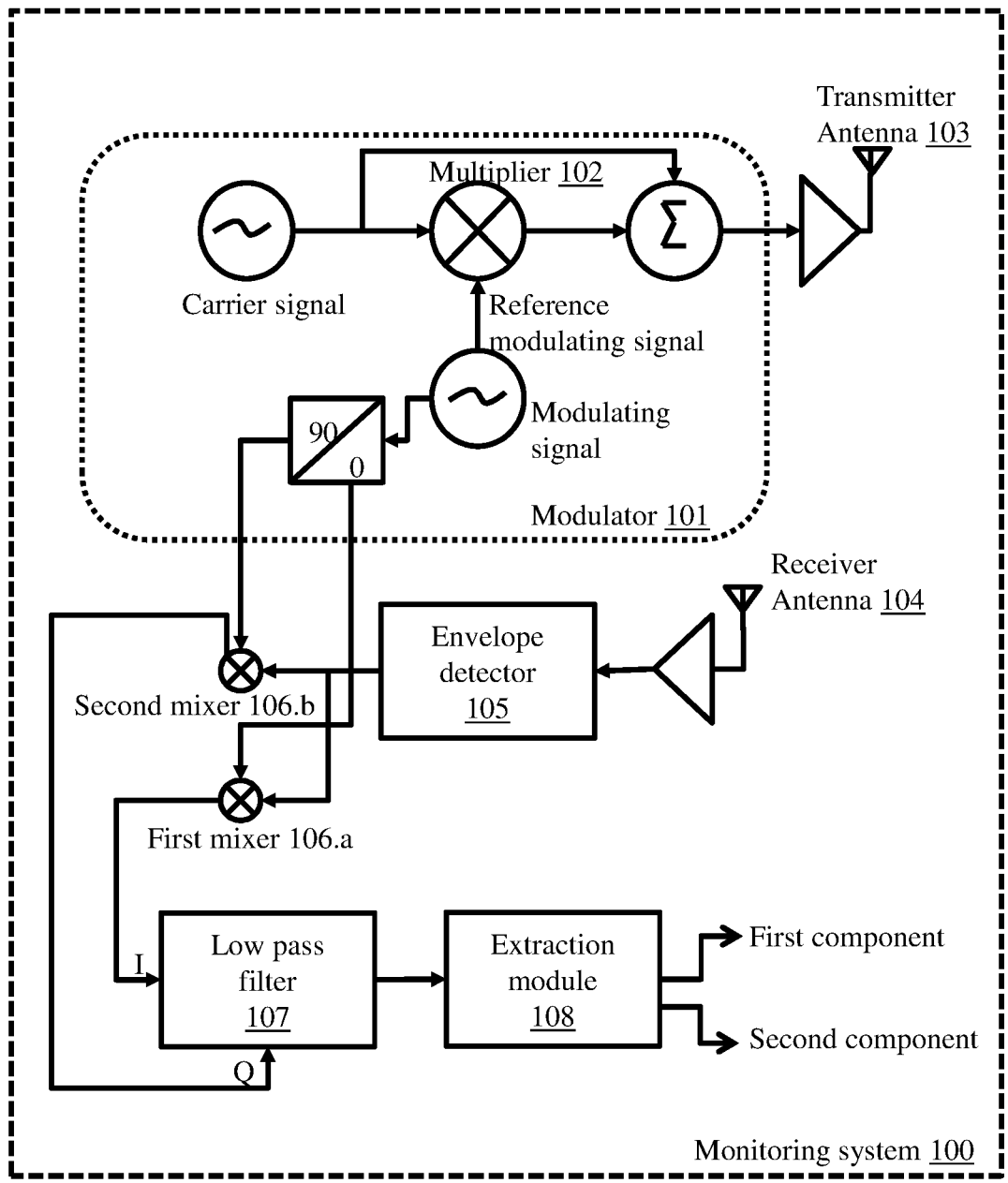
FIG. 1 illustrates an exemplary circuit diagram of a monitoring system used for health monitoring of a subject, according to some embodiments of the present disclosure.

FIG. 1 illustrates an exemplary circuit diagram of a monitoring system used for health monitoring of a subject, according to some embodiments of the present disclosure. The monitoring system (100), hereinafter referred to as 'system (100)' includes a modulator (101), an envelope detector (105), a transmitter antenna (103), a receiver antenna (104), a first mixer (106.a), a second mixer (106.b), a low pass filter (107), and an extraction module (108). The modulator (101) comprises of a multiplier (102).

The modulator (101) fetches a carrier signal and a modulating signal. Wavelength of the modulating signal is termed as 'probing wavelength'. The modulator (101) amplitude modulates (AM) the carrier signal i.e. amplitude of the transmitted signal is varied according to the modulating signal. The AMCW microwave signal is transmitted towards a subject (a user) being monitored, using the transmitter antenna (103). The transmitted AMCW microwave signal $T'(t)$ is represented as:

$$T'(t) = A_c \left[ 1 + \frac{A_m}{A_c} \cos(2\pi f_m t) \right] \cos(2\pi f_c t) \quad (1)$$

where $f_c$ and $f_m$ be carrier frequency and modulating frequency respectively. $A_c$ and $A_m$ are corresponding amplitudes.

The AMCW microwave signal reflects back from the subject, and the reflected signal is captured by the system (100), using the receiver antenna (104). The captured reflected signal $R'(t)$ is represented as:

$$R'(t) = A_c \left[ 1 + \frac{A_m}{A_c} \cos(2\pi f_m t - \Phi) \right] \cos(2\pi f_c t - \Phi) \quad (2)$$

where '$\Phi$' represents phase shift of the reflected signal as compared to the transmitted signal.

$\Phi$ depends on initial distance (i.e. distance between the transmitted antenna 103 and the subject) as well as on vital sign vibration x(t), and the relation is expressed as:

$$\phi = \frac{4\pi d}{\lambda} = \frac{4\pi d_0}{\lambda} + \frac{4\pi x(t)}{\lambda} = \Phi_{d0} + \Phi_{x(t)} \quad (3)$$

where, $$x(t) = m_r \sin(\omega_r t) + m_h \sin(\omega_h t) \quad (4)$$

where $m_r$ and $m_h$ are amplitude of breathing rate and heart rate of the subject, respectively. Similarly, $\omega_r$ and $\omega_h$ are frequency of breathing rate and heart rate of the subject, respectively.

In order to eliminate the harmonics, the system 100 makes final output of the system (100) proportional to the vital signal vibration x(t). For this purpose, the captured reflected signal $R'(t)$ is quadrature demodulated to generate a baseband in-phase output (I) and a quadrature phase (Q) output.

'Q' is Generated by:

Mixing the extracted modulating signal with a reference modulating signal. Here the reference signal is the modulating signal that had been transmitted towards the subject using the transmitter antenna (103). Q is represented as:

$$Q(t) = \frac{A_m^2}{2} \sin(\Phi_{d0} + \Phi_{x(t)}) \quad (5)$$

I is Generated by:

Introducing a 90 degree phase shift in the reference modulating signal, and further by mixing the 90 degree phase shifted reference modulating signal with the extracted modulating signal. I is represented as:

$$I(t) = \frac{A_m^2}{2} \cos(\Phi_{d0} + \Phi_{x(t)}) \quad (6)$$

Now:

$$\frac{Q(t)}{I(t)} = \tan^{-1}\left(\frac{\sin(\Phi_{d_0} + \Phi_{x(t)})}{\cos(\Phi_{d0} + \Phi_{x(t)})}\right) = (\Phi_{d0} + \Phi_{x(t)}) \quad (7)$$

Where $\Phi_{d_0}$ is a constant and can be removed.

Further the system 100 low pass filters the signals I and Q and then takes Arctangent (also referred to as 'Arctan' throughout the specification and claims) on ratio of output of the low pass filtering of the I and the Q using the low-pass filter 107, to capture relative phase shift of the signals, and to generate a relative phase shift signal.

Further the system 100 extracts a first component and a second component from the relative phase shift signal, wherein the first component represents the heart rate measurement and the second component represents the breathing rate measurement of the subject being monitored. In the process of extracting the first and the second components, the extraction module 108 obtains Fast Fourier Transform (FFT) of the relative phase-shifted signal. After obtaining the FFT, the extraction module 108 checks for dominant peaks in the obtained FFT. If any dominant peak is identified in 0.05 Hz to 1 Hz range in the obtained FFT, it is identified as a measured Breathing Rate. Similarly if any dominant peak is identified in 0.8 Hz to 2.5 Hz range in the obtained FFT, it is identified as the measured Heart Rate, by the system 100.

Figure 2A:
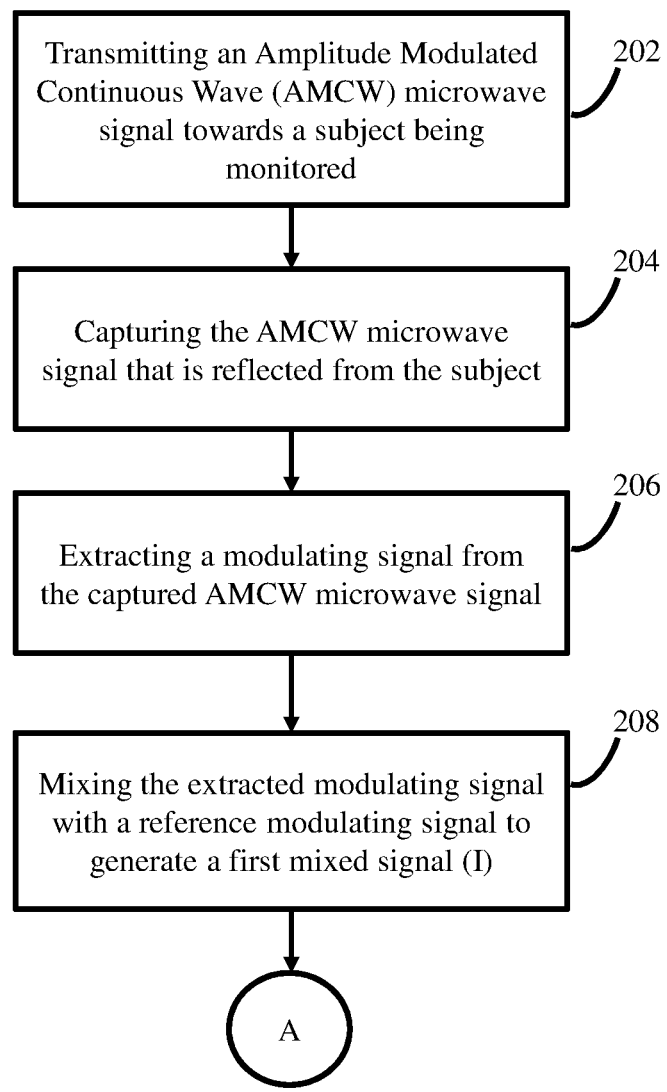
FIG. 2 (including FIG. 2A and FIG. 2B) is a flow diagram depicting steps involved in the process of health monitoring, using the monitoring system 100 of FIG. 1, according to some embodiments of the present disclosure.
Figure 2B:
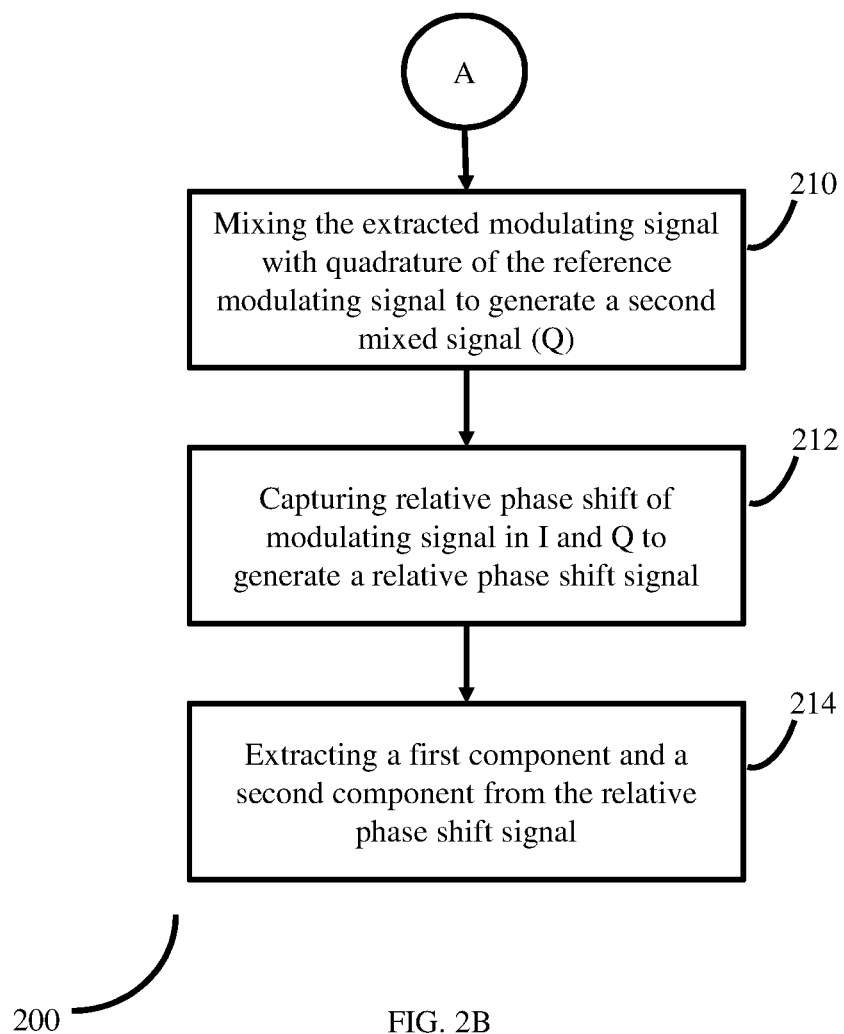

FIG. 2 (including FIG. 2A and FIG. 2B) is a flow diagram depicting steps involved in the process of health monitoring, using the monitoring system 100 of FIG. 1, according to some embodiments of the present disclosure. In the process of health monitoring using the monitoring system 100, initially an AMCW microwave signal is transmitted (202) towards the subject, and the AMCW microwave signal that is reflected from the subject is captured (204). From the captured signal, a modulating signal is extracted (206). The modulating signal is mixed (208) with a reference modulating signal to generate a first mixed signal (I). Further, the modulating signal is mixed (210) with quadrature of the reference modulating signal to generate a second mixed signal. Then the system 100 captures (212) relative phase shift of modulating signal in I and Q to generate a relative phase shift signal, and from the relative phase shift signal, a first component and a second component are extracted, wherein the first component represents the heart rate measurement and the second component represents the breathing rate measurement of the subject being monitored.

Figure 3:
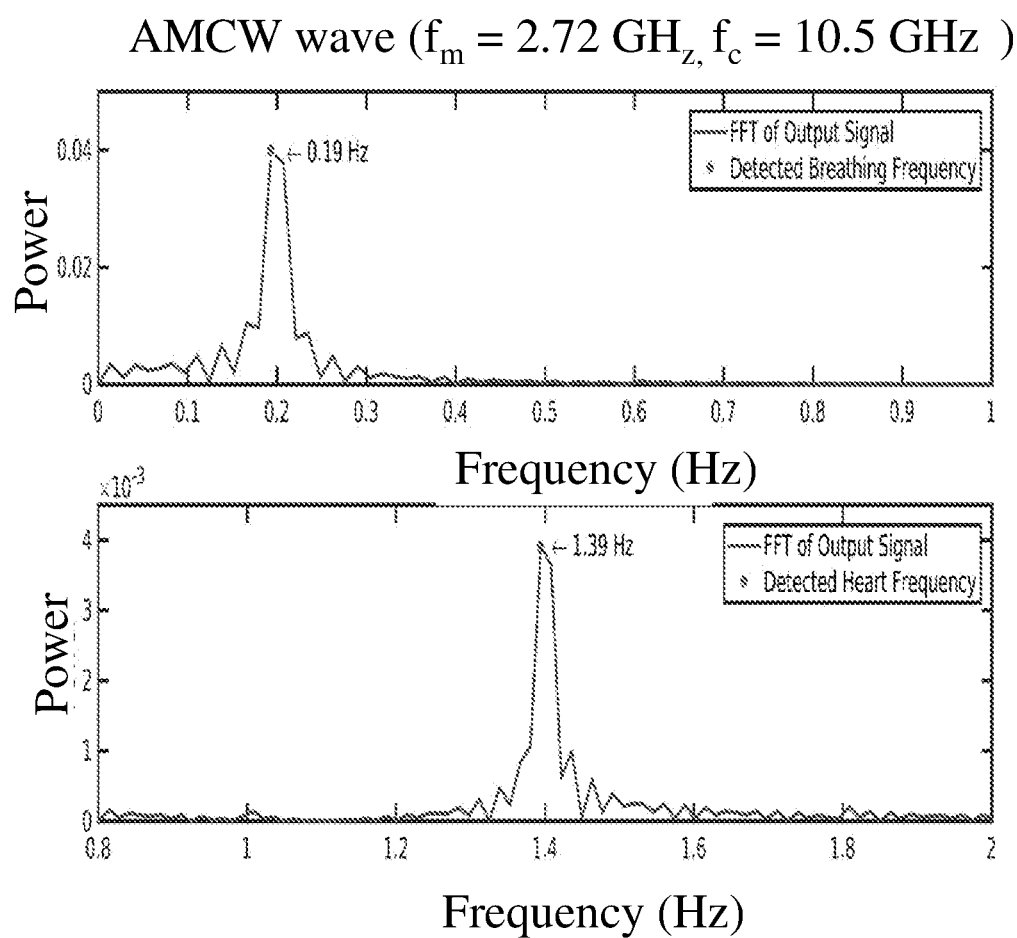
FIG. 3 is graphical representation depicting detection of Heart rate and Breathing rate when a carrier frequency of 10.5 GHz used by the monitoring system, according to some embodiments of the present disclosure.

Experimental Results:

In the experiment conducted, ground truths used are: Heart Rate (HR)=1.3 Hz (78 beats/second), amplitude of HR (mh) is 0.4 mm, Breathing Rate (BR) is 0.3 Hz (18 beats/min) and amplitude of BR (mr) is 4 mm. AMCW radar with modulating signal fm=2.72 GHz and fc=10.5 GHz with I/O based arctangent demodulation technique. In this experimental setup, distance between the subject and the radar is kept near to null point. This is depicted in FIG. 3, and it shows that the two components i.e. the breathing rate and the heart rate have been detected correctly.

As part of the experiment, when the carrier frequency was increased from 10.5 GHz to 24.05 GHz, the monitoring system 100 could detect the breathing rate and the heart rate.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method (200) for health monitoring, comprising:
transmitting (202) an Amplitude Modulated Continuous Wave (AMCW) microwave signal towards a subject being monitored, by a monitoring system, wherein the AMCW signal comprises a Continuous Wave (CW) microwave signal as a carrier signal along with a modulating signal;
capturing (204) the AMCW microwave signal when the AMCW microwave signal is reflected from the subject, by the monitoring system, wherein the modulating signal of the reflected AMCW microwave signal carries a measured heart rate and a measured breathing rate of the subject;
extracting (206) the modulating signal from the captured AMCW signal, by the monitoring system;
mixing (208) the extracted modulating signal with a reference modulating signal to generate a first mixed signal by the monitoring system, wherein the reference modulating signal is the modulating signal that is transmitted towards the subject, wherein a second signal is derived based on the reference modulating signal;
mixing (210) the extracted modulating signal with the reference modulating signal, by the monitoring system, after the extracted modulating signal and the reference modulating have been received by a quadrature receiver to generate a base band in-phase (I) and a quadrature phase (Q) output;
capturing (212) relative phase shift of the modulating signal in the first mixed signal and in the second mixed signal to generate a relative phase shift signal, by low pass filtering the first mixed signal and the second mixed signal and by taking Arctan on ratio of output of the low pass filtering of the first mixed signal and the second mixed signal, by the monitoring system;
eliminating harmonics by making a final output proportional to a vital signal vibration, wherein the captured AMCW signal is quadrature demodulated based on the generated base band in-phase (I) and a quadrature phase (Q) output;

and extracting (214) a first component and a second component from the generated relative phase shifted signal, by the monitoring system, wherein the first component represents the measured heart rate and the second component represents the measured breathing rate of the subject.

2. The method as claimed in claim 1, wherein a frequency of the carrier signal is used as base for designing an antenna size being used for transmitting the AMCW microwave signal towards the subject.

3. The method as claimed in claim 1, wherein extracting the first component and the second component comprises:
Obtaining a Fast Fourier Transform (FFT) of a relative phase-shift signal;
identifying a dominant peak in a 0.05 Hz to 1 Hz range in the obtained FFT as the measured Breathing Rate; and
identifying a dominant peak in a 0.8 Hz to 2.5 Hz range in the obtained FFT as the measured Heart Rate.

4. A monitoring system (100), comprising:
a modulator (101);
an envelope detector (105);
a transmitter antenna (103);
a receiver antenna (104);
a first mixer (106.$a$);
a second mixer (106.$b$);
a low pass filter (107); and
an extraction module (108);
wherein the monitoring system (100) is configured to perform health monitoring of a subject, by:
transmitting an Amplitude Modulated Continuous Wave (AMCW) microwave signal towards a subject being monitored, using the transmitter antenna (103), wherein the AMCW signal comprises a Continuous Wave (CW) microwave signal as a carrier signal along with a modulating signal;
capturing the AMCW microwave signal when the AMCW microwave signal is reflected from the subject, using the receiver antenna (104), wherein the modulating signal of the reflected AMCW microwave signal carries a measured heart rate and a measured breathing rate of the subject;
extracting the modulating signal from the captured AMCW signal, using the envelope detector (105) of the monitoring system;
mixing the extracted modulating signal with a reference modulating signal to generate a first mixed signal (I), using a first mixer (106.$a$) of the monitoring system, wherein the reference modulating signal is the modulating signal that is transmitted towards the subject, wherein a second signal is derived based on the reference modulating signal;
mixing the extracted modulating signal with the quadrature of the reference modulating signal, using a second mixer (106.$b$) of the monitoring system, after the extracted modulating signal and the reference modulating have been received by a quadrature receiver to generate a base band in-phase (I) and a quadrature phase (Q) output;
capturing relative phase shift of the modulating signal in the first mixed signal and in the second mixed signal to generate a relative phase shift signal, by low pass filtering the first mixed signal and the second mixed signal and by taking Arctan on ratio of output of the low pass filtering of the first mixed signal and the second mixed signal using the low-pass filter (107);
eliminating harmonics by making a final output proportional to a vital signal vibration, wherein the captured AMCW signal is quadrature demodulated based on the generated base band in-phase (I) and a quadrature phase (Q) output;
and
extracting a first component and a second component from the generated relative phase shifted signal, using the extraction module (108), wherein the first component represents the measured heart rate and the second component represents the measured breathing rate of the subject.

5. The monitoring system (100) as claimed in claim 4, wherein a frequency of the carrier signal is used as base for designing an antenna size being used for transmitting the AMCW microwave signal towards the subject.

6. The monitoring system (100) as claimed in claim 4, wherein the extraction module extracts the first component and the second component by:
Obtaining a Fast Fourier Transform (FFT) of a relative phase shift signal;
identifying a dominant peak in a 0.05 Hz to 1 Hz range in the obtained FFT as the measured Breathing Rate; and
identifying a dominant peak in a 0.8 Hz to 2.5 Hz range in the obtained FFT as the measured Heart Rate.

* * * * *